United States Patent [19]

Abel

[11] Patent Number: 5,056,515

[45] Date of Patent: Oct. 15, 1991

[54] TRACHEOSTOMY TUBE ASSEMBLY

[76] Inventor: Elaine R. Abel, 134 Fernwood Ave., Oroville, Calif. 95966

[21] Appl. No.: 637,603

[22] Filed: Jan. 4, 1991

[51] Int. Cl.$^5$ ............................................. A61M 16/00
[52] U.S. Cl. ............................ 128/207.15; 128/200.26
[58] Field of Search ....................... 128/200.26, 207.14, 128/207.15; 623/9

[56] References Cited

U.S. PATENT DOCUMENTS

| | | | |
|---|---|---|---|
| 2,087,493 | 4/1963 | Schosson | 128/207.15 |
| 3,039,469 | 6/1962 | Fountain | 128/200.26 |
| 3,169,529 | 2/1965 | Koenig | 128/207.14 |
| 3,616,799 | 11/1971 | Sparks | 128/207.15 |
| 3,693,624 | 9/1972 | Shiley et al. | 128/207.15 |
| 4,009,720 | 3/1977 | Crandall | 128/207.15 |
| 4,068,658 | 1/1978 | Berman | 128/200.26 |
| 4,304,228 | 12/1981 | Depel | 128/200.26 |
| 4,315,505 | 2/1982 | Crandall et al. | 128/200.26 |
| 4,449,523 | 5/1984 | Szachowicz et al. | 128/200.26 |
| 4,762,125 | 8/1988 | Leiman et al. | 128/207.15 |
| 4,819,664 | 4/1989 | Nazari | 128/207.15 |
| 4,852,565 | 8/1989 | Eisele | 128/207.14 |

Primary Examiner—Edgar S. Burr
Assistant Examiner—Aaron J. Lewis

[57] ABSTRACT

A tracheostomy tube assembly which includes a short, curved outer cannula affixed to a neck plate with strap, and a removable inner cannula having an affixed inflatable endotracheal cuff. When in use, the endotracheal cuff of the inner cannula is positioned beyond the terminal end of the outer cannula within the trachea. In a slightly varied embodiment of the invention, an accessory oxygen attachement is included for attachment to the outer cannula with the inner cannula and endotracheal cuff removed. The oxygen attachment is sized for releasable attachment over the outer exposed open end of the short outer cannula. The oxygen attachment is comprised a solid core plug having a narrow flexible air line positioned therethrough. The flexible air line is structured for attachment to an oxygen hose from an oxygen supply.

13 Claims, 6 Drawing Sheets

U.S. Patent     Oct. 15, 1991     Sheet 1 of 6     5,056,515
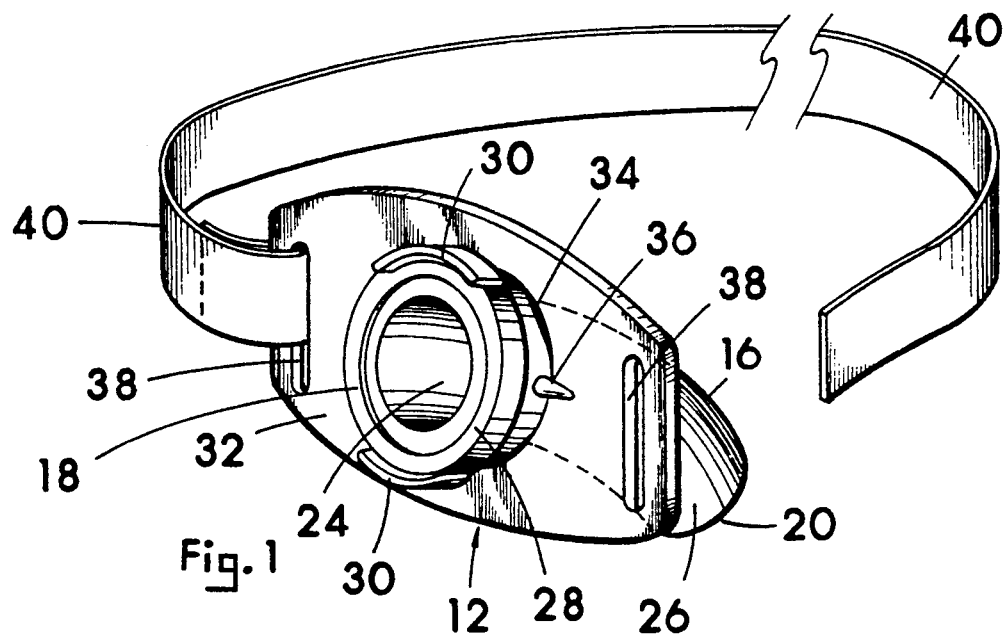
Fig. 1
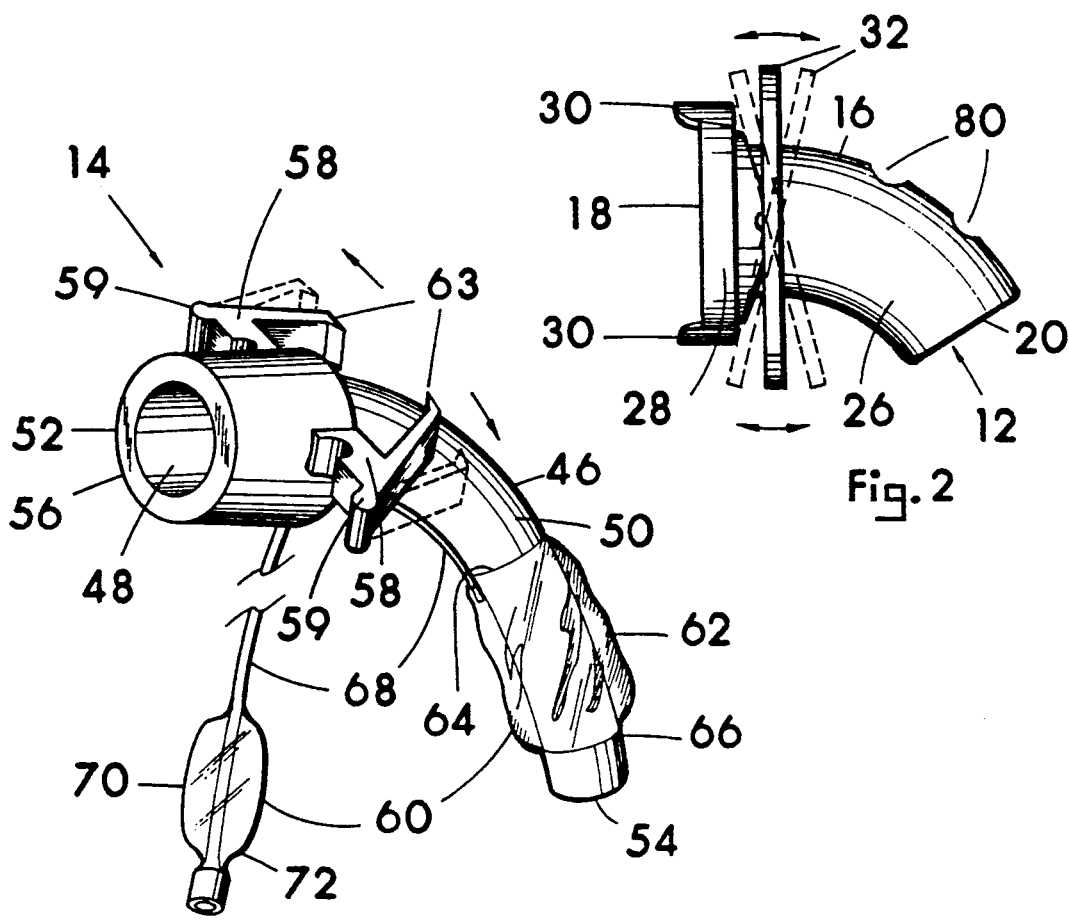
Fig. 2
Fig. 3

TRACHEOSTOMY TUBE ASSEMBLY

BACKGROUND OF THE INVENTION

1. Field of the Invention

This device is an improved tracheostomy tube assembly for human use, structured for respirator and oxygen supply attachments to help support breathing. This tracheostomy tube assembly is designed to significantly extend the length of time between cleaning of the outer cannula of the tracheostomy tube, greatly reduce irritation of the stoma, and also improve speech during oxygen therapy.

2. Description of the Prior Art

Tracheostomy tubes have been in use for some time for providing ventilation directly to the patient's trachea through an opening, or stoma, in the patient's throat. Existing tracheostomy tubes are generally comprised of an outer curved cannula with a removable inner cannula. The outer cannula is designed to remain inserted within the stoma to keep it patent, and contains an exterior plate with which it can be affixed around the neck with a tether, to prevent the cannula from becoming dislodged. The distal end of some outer cannulas of the past art is also affixed with an inflatable balloon, or endotracheal cuff, for closing off the trachea for ventilation by a mechanical respirator. The inner cannula is removable and is primarily designed for easy connection to a respirator, and for easy cleaning of the lumen of the tracheostomy tube. Tracheostomy tubes are provided in both metal and plastic units. Plastic units can also be reuseable or disposable items, with disposable items being the most popular.

The medical conditions which require tracheostomies vary considerably in their etiology and their severity. In some of the more serious conditions, the patient may not be able to breath unaided, and is therefore dependant on an artificial mechanical respirator for survival. Sometimes the patient's condition improves, and he is gradually weaned from the respirator and basically retrained to breath on his own. Oxygen therapy is often also required during some or all phases of treatment. Sometimes the tracheostomy tube must remain in place for the rest of the patient's life, while other times the surgery is reversed closing the stoma, and the patient resumes normal breathing. Therefore, there may exist a wide variety of pulmonary conditions which tracheostomy tubes must accommodate.

Current existing tracheostomy tube assemblies have problems associated with long term maintenance. One major problem is the occurrence of frequent or chronic infections in and around the stoma and within the trachea. The relatively long length of the existing outer cannulas provides greater surface area to retain secretions and therefore, infectious organisms. Some of the measures used to treat or prevent infections includes suctioning, and frequent replacement or cleaning of parts to remove the build up of secretions, and occasionally the administration of antibiotics. The replacement or cleaning procedure includes frequent removal, sometimes daily, of the inner cannula, with the outer cannula being removed much less often, generally at six week intervals. This cleaning procedure, especially of the outer cannula, can be very uncomfortable to the patient especially if the stoma and adjacent area is infected or irritated. The more infections that occur or persist, the more often the tracheostomy tube will generally be cleaned, which in turn further irritates the already sensitive tissue. Although the endotracheal cuff on the outer cannula is deflated prior to removal, the folds of the cuff also cause a great deal of discomfort as it is withdrawn from an irritated stoma. When in use and inflated, the endotracheal cuff also exerts significant pressure against the interior wall of the trachea, which over an extended period of time, is not only uncomfortable for the patient, but serious damage, such as necrosis of the tracheal wall, can eventually result. Currently, intermittent deflation of a permanent cuff is required to prevent damage of the tracheal lining. Some tracheostomy tubes even have two inflatable cuffs or balloons, which allows alteration of the pressure points by inflating each balloon at separate times.

The operation and maintenance of the tracheostomy tube can become a painful and tiring experience for the patient. Since the stoma has a tendency to close rather quickly when not kept patent by the outer cannula, the patient can become anxious during the cleaning procedure, or replacement of a new cannula, for fear of not having an adequate airway when the cannula is removed. When the patient experiences prolonged or chronic infections, his overall prognosis can be adversely affected by the persistent debilitating strain it causes.

Another disadvantage of the existing tracheostomy tubes is the threat of air leakage between the inner cannula and outer cannula, and therefore a tight seal must be maintained between the two. Since ventilation of a patient with a respirator necessitates a closed pressurized system, air leakage must be prevented around the inflated cuff, at the external connecting attachments, and also between the two cannulas.

The extended curvature of existing cannulas is basically generic, and often does not conform well to individual patient anatomies, resulting in one or more portions of the tube rubbing on the tracheal wall.

Patients not totally dependant on a respirator, often use oxygen attachments for administering oxygen directly into the trachea via a transtracheal oxygen tube from a portable oxygen tank. Most of the current oxygen attachments however, have the disadvantage of impairing the speech of the patient. One of the more common oxygen attachments looks similar in appearance to an oxygen mask, and is referred to as a tracheotomy mask. The tracheotomy mask is designed to fit over the outer cannula, and is secured in place with a tie which attaches the device around the neck of the patient. A transtracheal oxygen tubing is connected on one end to the mask, and the other end is generally attached to a portable oxygen tank. The major disadvantage of the tracheotomy mask is that the seal between the mask and tracheostomy opening is not complete and oxygen can escape around the edges of the mask. This system also does not provide back pressure for air escaping through the outer cannula when the person tries to speak. The patient must therefore cover the outer opening or lumen, generally with a finger, in order to force enough air through the vocal cords to produce speech. This procedure is awkward and inconvenient for the patient, requiring him to close off the opening every time he wishes to speak. There is also an increased risk of introducing germs into the trachea when the patient uses his or her fingers to obstruct the cannula opening.

A past art patent search was conducted to examine devices similar to my invention. Of those examined, the following were considered most relevant:

The D. P. Shiley et al patent, U.S. Pat. No. 3,693,624, issued on Sept. 26, 1972, represents the basic structure common to existing tracheostomy tubes, and is herein included as being representative of that particular group. Shiley teaches a Tracheotomy Tube, where the endotracheal cuff is affixed to the outer cannula instead of the inner cannula. The long length of the outer cannula, with affixed endotracheal cuff, provides extra surface area for accumulating infectious microbes. The Shiley et al device is in common use today and generally requires replacement or cleaning of the outer cannula at regular frequent intervals, commonly six weeks. The tube with which the cuff is inflated is also positioned on the exterior of the outer cannula and can create irritation to the patient, along with the deflated cuff, as the cannula is removed. There also must be a tight seal between the inner and outer cannulas since air leakage could result when the system is attached to a respirator.

The U.S. patent titled Fenestrated Tracheostomy Tube which was granted to R. F. Eisele, on Aug. 1, 1989, U.S. Pat. No. 4,852,565, incorporates air passages or fenestrations into the upper surface wall of the outer cannula for the purpose of weaning the patient from a respirator by providing breathing apertures when the inner cannula is removed and the patient is disconnected from the respirator. However, the previously mentioned disadvantages of the prior art are still present in this device.

Another disadvantage of the prior art is the possibility of the inflated cuff rupturing or leaking. Since the damaged cuffs must be replaced by removal of the outer cannula, this could be a serious situation when the patient is dependant on a respirator. Re-insertion of a new outer cannula can be a difficult procedure, often requiring a doctor, and in some hospitals, doctors are mandated to perform the procedure.

Therefore, all of the previously mentioned disadvantages of the past art, especially the susceptibility for creating infections although indirectly, contribute to the patient's slow recovery. In some cases the infection can even prove fatal. Therefore any modification in existing tracheostomy equipment that significantly reduces the chance of infection and reduces discomfort to the patient is considered to be an advantage.

My invention significantly decreases the occurrence of infections, reduces the recovery time when weaning a patient from a respirator, and increases the patient's comfort.

BRIEF SUMMARY OF THE INVENTION

My invention comprises an improved tracheostomy tube assembly which includes a short outer cannula pivotally affixed to a neck plate, and an elongated removable inner cannula. The second end of both cannulas are structured for insertion into the trachea, with the first ends positioned on the exterior of the patient's neck. The assembly is stabilized in use by way of the neck plate abutted against the exterior surface of the neck, and further with a tether extending around the neck and affixing back to the neck plate at two points. The second end of the inner cannula extends beyond the second end of the outer cannula. The second end of the inner cannula is affixed with an inflatable endotracheal cuff.

The outer cannula of the immediate invention is significantly shortened, in relation to the inner cannula, and there is no inflatable endotracheal cuff affixed to the second end of the outer cannula. With this reduced structure, the surface area has been decreased onto which infectious agents can accumulate, therefore reducing the incidence of acquired infections and increasing the length of time it can remain inserted within the stoma. The shorter length of the outer cannula is also more suitable to most patient anatomies than one which is relatively long. The outer cannula also contains fenestrations or apertures which help to allow exchange of air through the vocal cords when the inner cannula is removed and the opening to the outer cannula is sealed. When the outer cannula is used in conjunction with the accessory oxygen attachment developed for use with the present tracheostomy tube, this feature allows the patient improved speech capabilities.

The inner cannula is longer in length than the outer cannula, with the inflatable cuff affixed to the second end. The first end of the inner cannula is structured for releasable attachment to the outer cannula, and also contains a coupler for attachment to a respirator hose or line.

In-use, the outer cannula is positioned within the stoma and stabilized in place. The inner cannula is then inserted through the bore of the outer cannula and snapped onto the outer opening of the outer cannula. The endotracheal cuff is then inflated with air. Connections for use of a respirator are then made to the first end of the inner cannula. With the cuff inflated, air is forced into the patient's lungs, by the respirator, through the hollow interior of the inner cannula. Therefore a direct airway is established from the outer or first end of the inner cannula to the trachea, greatly reducing the possibility of air leakage between the inner cannula and the outer cannula. A relatively loose connection can therefore be made between the interior wall of the outer cannula with that of the exterior wall of the inner cannula since it is not a critical sealing area. Therefore, since a loose connection can be made between the inner and outer cannula walls, there is sufficient room for removal of the deflated cuff through the interior bore of the outer cannula. Should a leak occur in the cuff during connection to a respirator, a second replacement inner cannula can be quickly and easily inserted in minutes by a nurse, since the outer cannula would still be in position maintaining a patent stoma. This could prove to be a life saving measure in certain circumstances where a doctor who, mandated by certain hospital regulations, is himself required to insert existing cannulas and who may unfortunately be unavailable during such a crisis. In such a situation where the immediate invention is in use, a nurse can easily change the inner cannula should the balloon malfunction.

By reducing the length of the cannula, and reducing the use of the inflatable cuff, the occurrence of infection is greatly reduced. Since reducing the occurrence of infections is one main reason for frequent cleaning, it can therefore be done much less often, thus reducing the pain experienced by the patient during such procedures. Pain is also greatly reduced or eliminated during cleaning procedures when the infections are eradicated and the surrounding tissue is not inflamed. When secretions accumulate sufficiently on the tube, breathing can be hampered, which not only is a cause of anxiety to the patient but also further debilitates his condition by producing inefficient oxygen exchange. Even frequent suctioning can leave the patient tired. By adding the cuff to the inner cannula, the deflated cuff can be removed through the outer cannula, thus saving the patient the irritation of withdrawing the deflated cuff through the stoma. Even though the deflated cuff is comprised of relatively soft pliable plastic, irregular edges still exist, once deflated, and those edges can be a source of irritation especially if the patient's stoma is inflamed. The patient is therefore saved this discomfort by the deflated cuff being withdrawn through the outer cannula.

If a patient is not totally dependant on the respirator, the inner cannula with cuff can be removed at certain times, thus occasionally relieving the pressure exerted on the tracheal wall by the inflated cuff. This helps to prevent irritation and the break down of the lining of the trachea. In the past art, the cuff is affixed to the outer cannula and since the outer cannula must remain in place at all times, except for cleaning, the inflated cuff exerts pressure against the tracheal wall for a much longer period of time than that of the current invention. Removing the outer cannula for more than a few hours can result in the stoma closing permanently, therefore it must remain in position generally continuously, except for cleaning. By reducing the occurrence of infection, the present invention can remain in position within the tracheas for a much longer period of time, up to a year in some circumstances, as compared to the average of six weeks for similar past art devices.

When the patient is disconnected from the respirator, and the inner cannula removed, the outer cannula is still maintained in position with a tether about the patient's neck. Since maintaining the patency of the stoma is a primary purpose of the outer cannula, and since an attachment tether is already used on the outer cannulas of both the present invention and many past art devices, the necessity of placing the cuff or balloon on the outer cannula as a secondary back-up attachment, as in the past art, is really not necessary. Displacement of the outer cannula is rare and there is the neck tether to prevent this occurrence. Even if the outer cannula of this invention were inadvertently displaced from the stoma, the shortened length of the cannula would make it much quicker and easier to reinsert than one of extended length.

For administration of oxygen therapy for patients not dependant on a respirator, I have provided an accessory oxygen attachment comprised of an attachable plug with an inherent air hose or line, the plug being sized for sealingly closing off the aperture of the outer cannula. The air line is a very small flexible plastic tubing which extends up through the bottom edge of the plug, curving through the center and exiting the back, finally projecting down into the interior of the outer cannula. The exterior tubing entering the front lower edge of the plug is structured for attachment to an oxygen hose. One novel feature of this device is it allows the patient a continuous supply of oxygen even while he speaks, without the patient required to close off the open first end of the outer cannula. The reduced size of the outer cannula, along with the fenestrations, provides sufficient room for air to pass through and around the outer cannula and out through the larynx, enabling the patient to speak with the transtracheal oxygen attachment in place. Also, the structure of my accessory oxygen attachment provides a sufficiently low profile to allow the patient to wear turtle neck sweaters or tie a scarf about the neck without kinking the oxygen line. Some patients are self-conscious about their tracheostomies and would prefer them to be hidden from view. The more normal speech and appearance that the patient can maintain, the more comfortable he will be. His general outlook will be better and his attitude more optimistic, which has proven to be a favorable aspect in the recovery of any patient. Therefore, providing the patient with equipment which allows him to maintain a more normal way of life is always desired.

The outer cannula is provided in several sizes or length variations for accommodating the differing neck thicknesses of patients. A very heavy patient would have excess tissue on the outer surface of the trachea, that a thin person would not and thus would require a longer outer cannula.

The neck plate affixed to the outer cannula of this invention is manufactured of a generally rigid plastic, and functions well to provide a comfortable fit to the patient's neck due to the pivotal attachment of the neck plate to the outer cannula. However, in the absence of a pivotal attachment between the neck plate and the outer cannula, I recommend a soft, flexible plastic for the material of manufacture of the neck plate. This conformability, whether from a flexible neck plate or a pivotal attachment thereof to the outer cannula allows a better fit which is more comfortable to the patient.

Therefore, a primary object of my invention is to provide a tracheostomy tube assembly which reduces the occurrence of infection and pain.

Another object of the invention is to provide the above in a tracheostomy tube assembly which can be worn for an extended period before requiring cleaning.

A further object of the invention is to provide the above in a tracheostomy tube assembly which eliminates the pain and the irritation of the stoma due to removal of a portion of the assembly.

An even further object of the invention is to provide the above in a tracheostomy tube assembly which includes a removable inner cannula having an endotracheal cuff which reduces the irritation to the lining of the trachea from prolonged inflation of the cuff.

Another object of the invention is to provide the above in a tracheostomy tube assembly having an endotracheal cuff capable of quick and easy replacement by a health care worker.

A still further object of the invention is to provide the above which, with the inner cannula having the inflatable cuff removed, allows for the simple attachment of a transtracheal oxygen attachment to the outer cannula.

Other objects and advantages of the invention will become apparent by reading the remaining specification and examining the accompanying drawings.

BRIEF DESCRIPTION OF THE DRAWINGS

FIG. 1 is a perspective frontal view of the neck plate and outer cannula of the invention;

FIG. 2 is a side view thereof;

FIG. 3 is a frontal perspective view of the inner cannula with the inflatable cuff of the invention;

DESCRIPTION OF THE PREFERRED EMBODIMENTS

Figure 4:
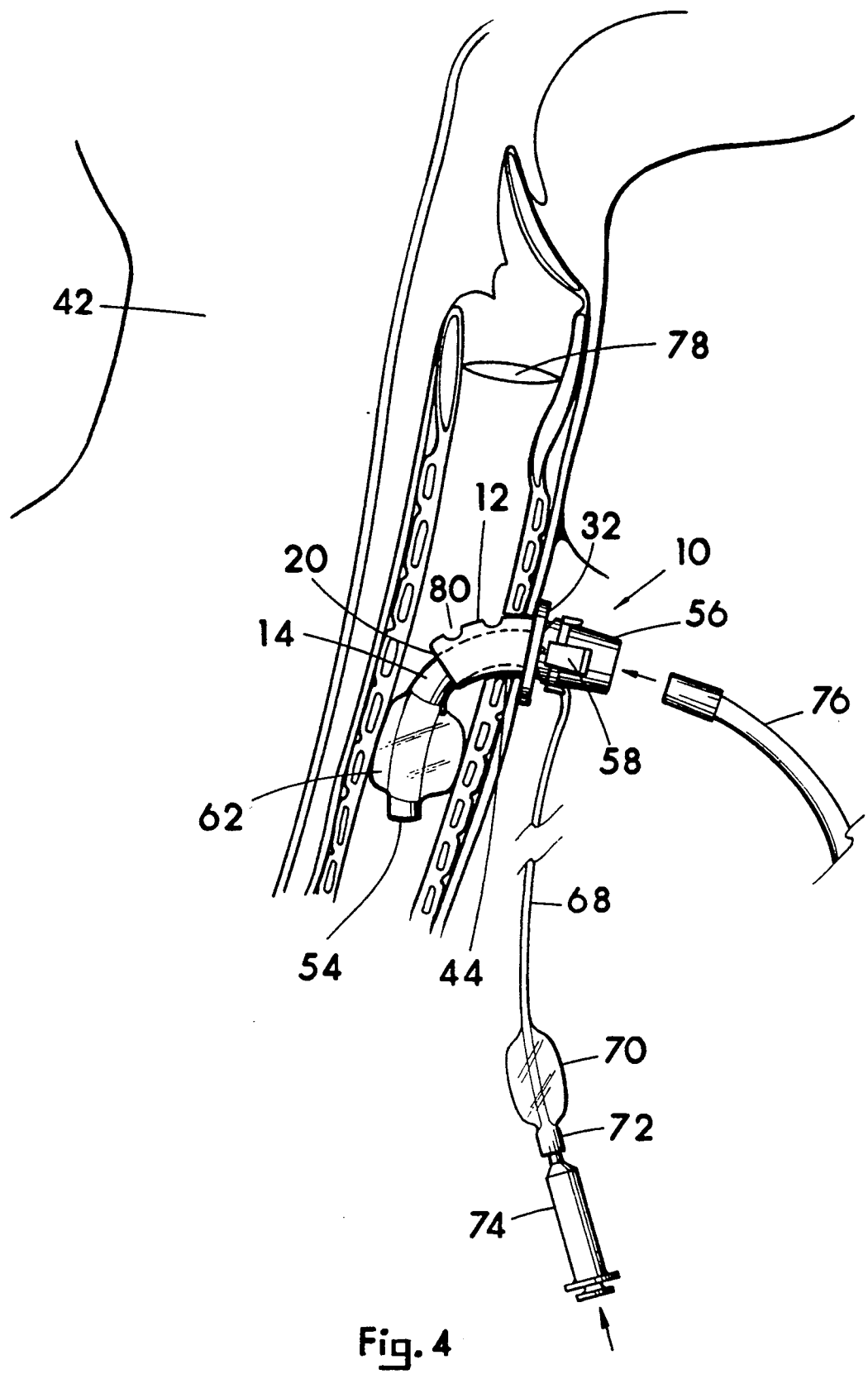
FIG. 4 depicts the assembled tracheostomy tube in position through the stoma into the trachea. An air syringe is shown inflating the endotracheal cuff, and a respirator air line is shown in position for attachment to the first end of the inner cannula.
Figure 5:
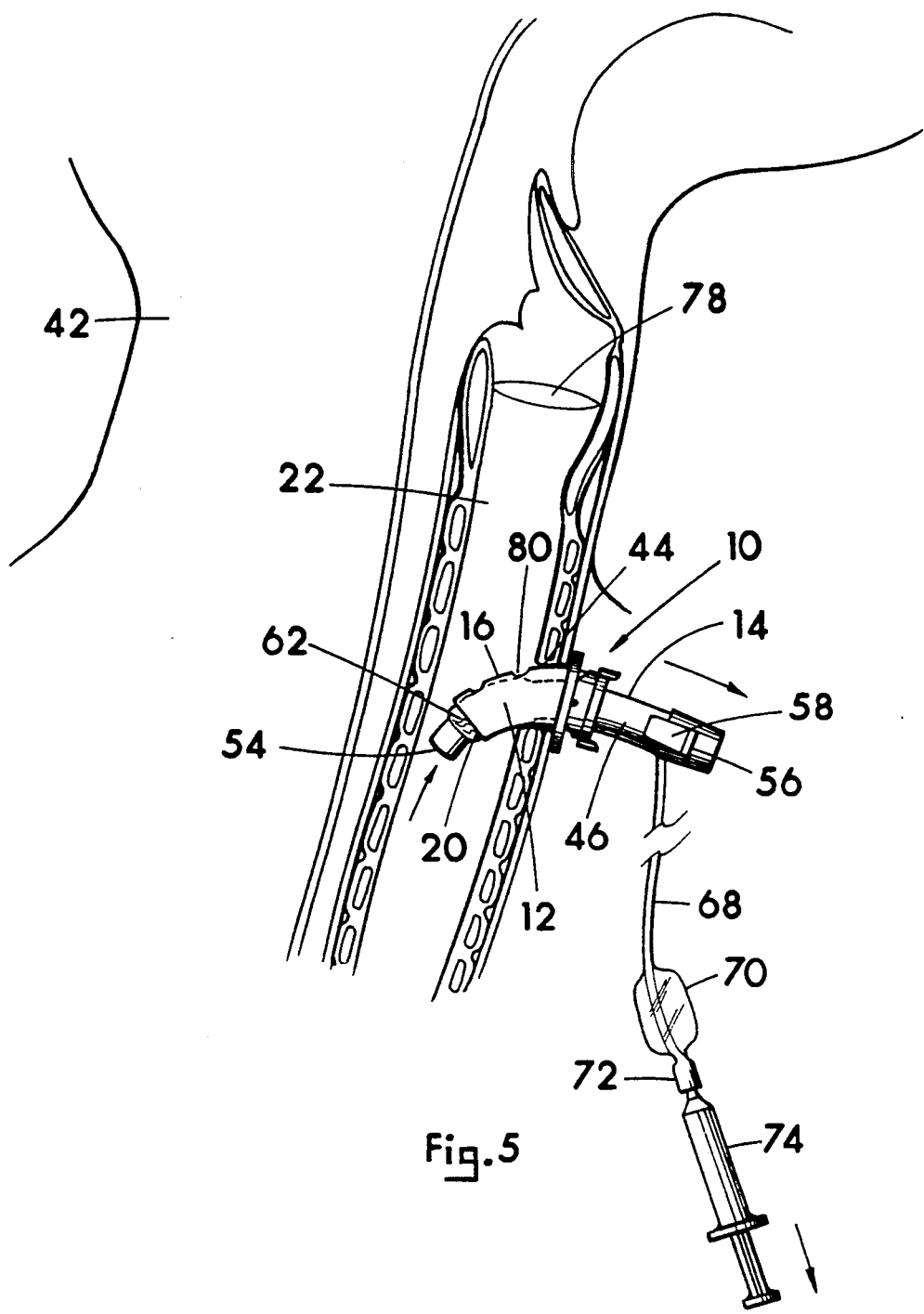
FIG. 5 depicts the inner cannula with deflated cuff, being withdrawn from the outer cannula.
Figure 6:
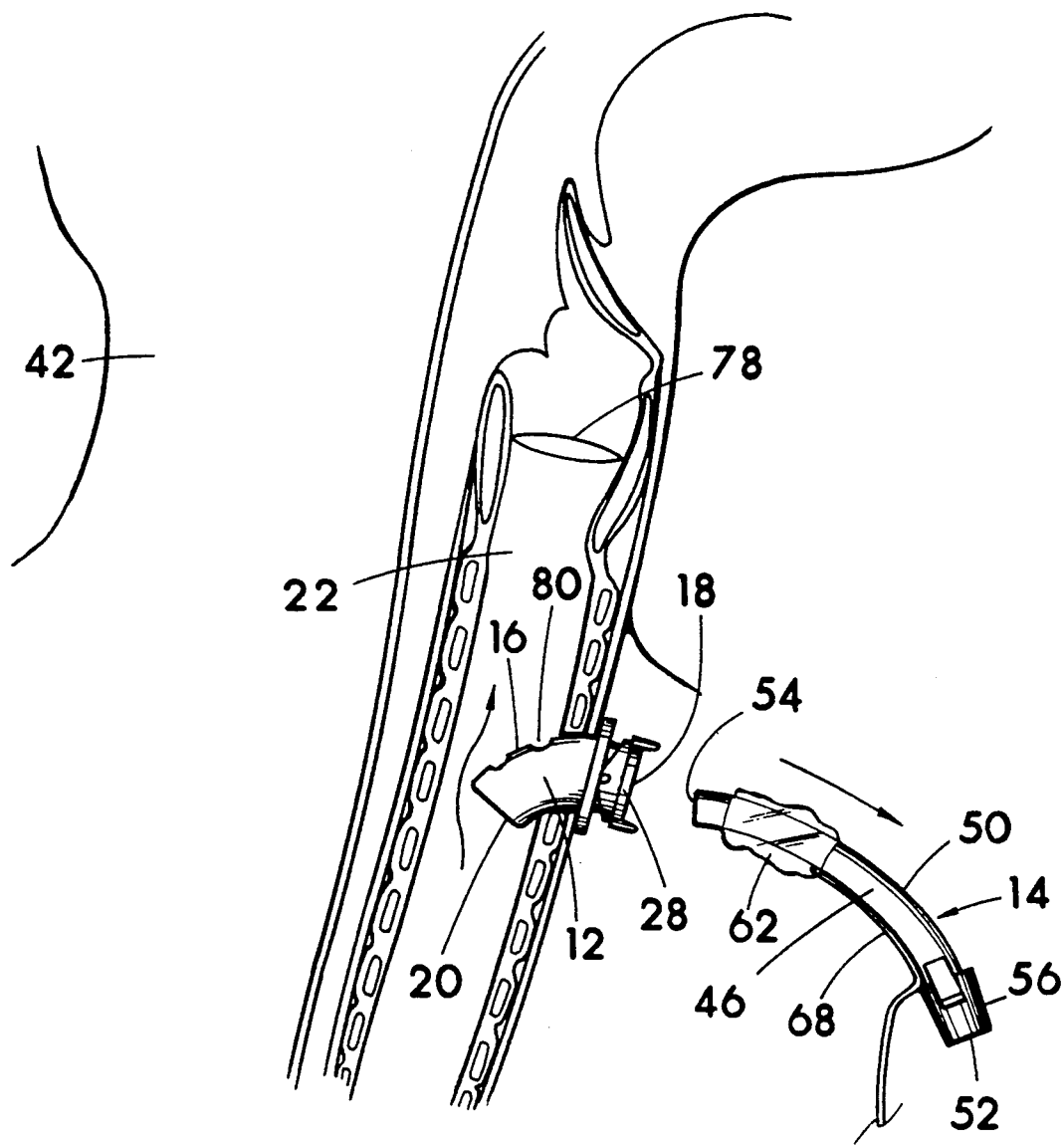
FIG. 6 shows the inner cannula with deflated cuff completely removed from the outer cannula.

Referring to the drawings where tracheostomy tube assembly 10 is illustrated. Tracheostomy tube assembly 10 is comprised of outer cannula 12, shown in FIG. 1 and 2, and an inner cannula 14, shown in FIG. 3. Preferably tracheostomy tube assembly 10 is comprised of plastic, but can also be manufactured of metal. Outer cannula 12 is comprised of an arcuate tubular body 16 having a open first end 18 and a open second end 20, with the second end 20 positioned inside of a trachea 22 when in use. First end 18 is positioned on the exterior of the patient for connection of accessory equipment. Outer cannula 12 also has an interior lumen 24 and an exterior outer wall 26, which contains several fenestrations 27. Fenestrations 27 are small apertures located on the upper central surface of outer cannula 12 which allow exchange of air between the lungs and the patient's vocal cords. Inherently affixed to the edge of open first end 18 is attachment rim 28. Attachment rim 28 is an enlarged flanged edge with two opposing stabilizers 30. Each stabilizer 30 is a short narrow tab projecting outward from the surface of attachment rim 28, structured to stabilize the attachment of inner cannula 14. Pivotally affixed just behind attachment rim 28 is neck plate 32. Neck plate 32 is basically a rectangular flattened plate having a central aperture 34 through which outer cannula 12 is positioned. Attachment of neck plate 32 onto outer cannula 12 is made with two pivotal tabs 36. The outer ends of neck plate 32 contain two elongated vertical loops 38, through which tether 40 can be affixed. Tether 40 can be a flexible strap or cloth tie for securing neck plate 32 flush against the surface of neck 42, thereby maintaining body 16 of outer cannula 12 within stoma 44. Tether 40 is shown in FIG. 1 as a single band of flexible material, one end of which is affixed to one loop 38 with the free end to be manually tied to the second loop 38.

Inner cannula 14 is comprised of an elongated arcuate tubular member 46 sized for removable insertion into the lumen 24 of outer cannula 12. Inner cannula 14 also has an interior lumen 48, an exterior wall 50, an open first end 52, and an open second end 54. Affixed to open first end 52 is a short tubular coupler 56. The proximal edge of coupler 56 is affixed with two inherently spring biased clamps 58, positioned one on either side of coupler 56. Each clamp 58 is roughly comprised of an elongated wedge shaped member affixed by a flexible post to coupler 56. The distal end of the wedge shaped member is referred to as attachment end 61 and the opposite end is referred to as gripping knob 59. When inner cannula 14 is inserted into outer cannula 12, attachment ends 61 snap over attachment rim 28 by manually pressing both gripping knobs 59 toward each other. Attachment of attachment ends 61 over attachment rim 28 secures both cannulas 12 and 14 together.

Affixed adjacent to second end 54, on exterior wall 50 of inner cannula 14, is an inflatable endotracheal cuff 60. Endotracheal cuff 60 includes a clear flexible balloon 62, the terminal ends, first end 64 and second end 66, are affixed to exterior wall 50 of inner cannula 14. Balloon 62 is inflated with inflation tube 68, which is a thin hollow flexible tube which extends from the interior of balloon 62 up along exterior wall 50, and projects unattached just before coupler 56. The free end of inflation tube 68 is connected to pilot balloon 70 and check valve 72. Pilot balloon 70 is a small inflatable bladder positioned on the distal end of inflation tube 68, exterior of the patient's neck 42 when in use. Pilot balloon 70 inflates directly in relation to balloon 62, and any leakage in the system will be evident in pilot balloon 70. Check valve 72 is a self sealing valve allowing inflation of balloon 62 with a syringe 74, preferably with air although sterile water can also used. Air can also with withdrawn from balloon 62 with syringe 74 in order to deflate balloon 62 and remove inner cannula 14. Balloon 62, inflation tube 68, pilot balloon 70 and check valve 72 are referred to in composite as endotracheal cuff 60. Coupler 56 of inner cannula 14 is structured for releasable attachment, by way of a resistance fit or other suitable attachment structure, to a ventilator hose or line 76 which is connected to a ventilator or respirator.

In-use, body 16 of outer cannula 12 is inserted, second end 20 first, into stoma 44 located on the patient's neck 42 below larynx 78. To secure outer cannula 12 in position, the terminal ends of tether 40 are affixed to each open loop 38 of neck plate 32 and releasably connected together, positioning neck plate 32 flush against neck 42. Tether 40 is shown in the drawings as a flexible strap, preferably soft material, with one end permanently affixed to one loop 38 of neck plate 32 and the opposite end of tether 40 left free for manually tieing onto the second loop 38. Other methods of attachment of tether 40 are also possible.

To assemble tracheostomy tube assembly 10, tubular member 46 of inner cannula 14 is inserted, second end 54 first, into the open first end 18 of outer cannula 12. Tubular member 46 is advanced until coupler 56 abuts attachment rim 28 of outer cannula 12. Clamps 58 are then locked around attachment rim 28, with the outer edges of coupler 56 further secured by stabilizers 30. Syringe 74, filled with a pre-measured volume of air, is inserted into check valve 72, where the air is injected into balloon 62 through inflation tube 68. Pilot balloon 70 is also simultaneously inflated along with balloon 62, and serves as a safety check measure to assure balloon 62 is always inflated. Syringe 74 is then removed from connection with check valve 72, but always kept close by incase of emergency. Ventilator line 76, connected to a respirator, not shown, is then connected to coupler 56. Various types of releasable connections, well known to those skilled in the art, can be used for attachment of ventilator line 76 to coupler 56. Respirators generally work on the principal of intermittent positive pressure breathing where the lungs are inflated at regular intervals by providing air in positive pressure. To accomplish this, there must be a closed one-way system from the respirator to the lungs, with the generally passive expirations being exhausted through the ventilating system and not the patient's mouth or nose. Leakage must be prevented through all connections of the system, which in this invention are reserved to the connection between coupler 56 and ventilator line 76, and balloon 62 and the interior walls of trachea 22.

To remove inner cannula 14, for cleaning or for allowing the patient to breath on his own, disconnection is first made between ventilator line 76 and coupler 56. Balloon 62 is then deflated with the use of syringe 74.

Clamps 58 can then be released by pressing both gripping knobs 59 toward each other, thus drawing attachment ends 61 outward, as shown in FIG. 3, away from engagement with attachment rim 28 of outer cannula 12. Tubular member 46 of inner cannula 14 is then removed from the interior of outer cannula 12. Outer cannula 12 still remains in position with the use of tether 40. The patient can still speak, if he is able to breath unaided, since air is allowed free passage around outer cannula 12 and through fenestrations 27. Fenestrations 27 are merely openings made into the top of outer wall 26 which allow passage of air up through larynx 78.

Figure 7:
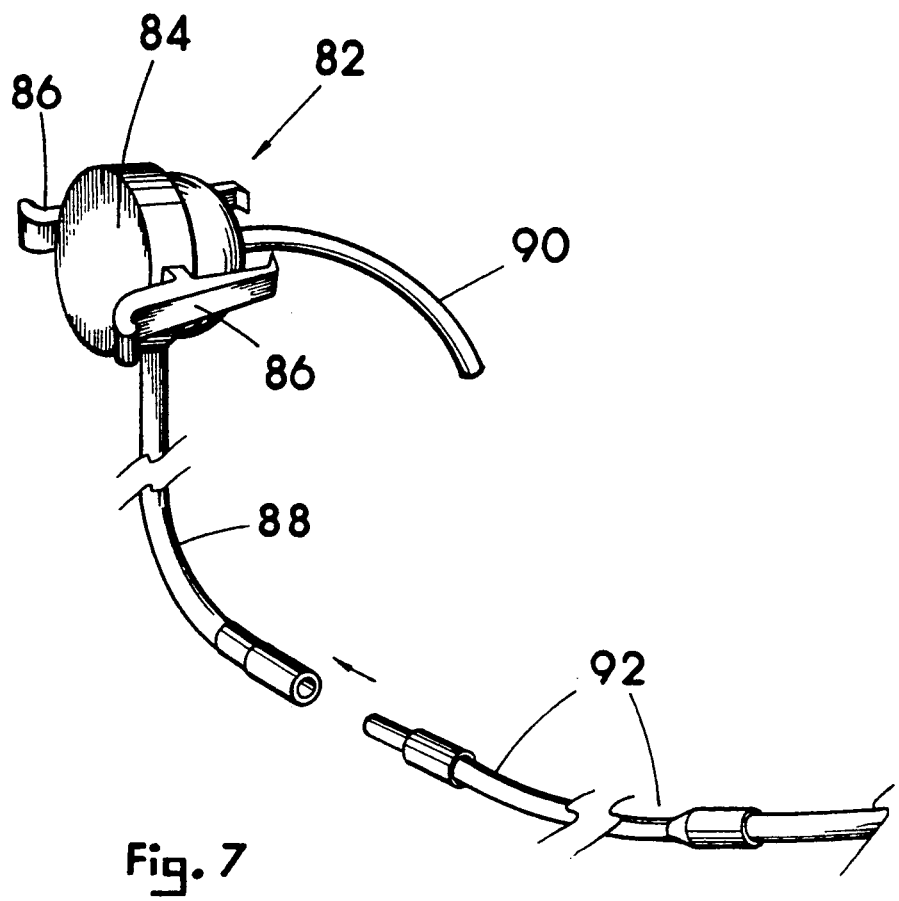
FIG. 7 is a frontal perspective view of the oxygen attachment of the invention positioned for attachment to transtracheal oxygen tubing.
Figure 8:
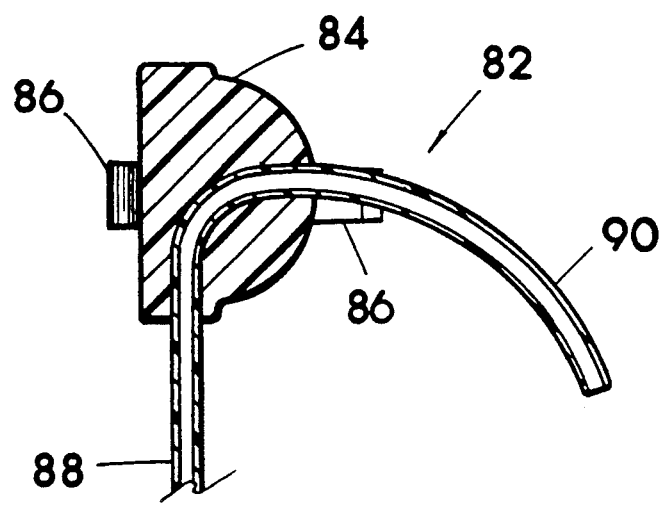
FIG. 8 is a cross-sectional side view of the oxygen attachment shown in FIG. 7.
Figure 9:
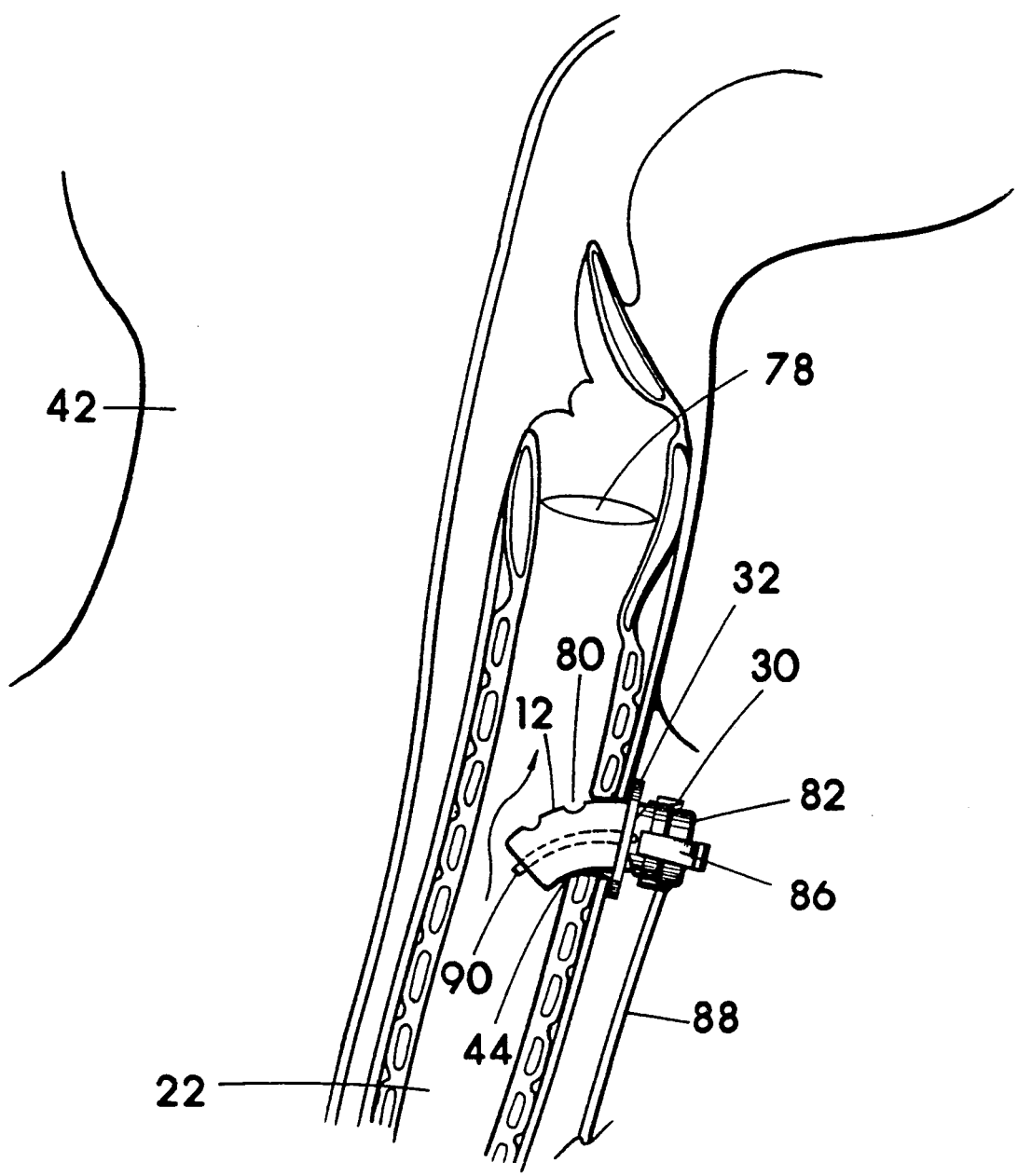
FIG. 9 depicts the oxygen attachment in use affixed to the outer cannula shown in FIG. 1.

Should the patient require oxygen therapy during this stage of the procedure, I have provided an improved oxygen attachment 82, for connection to a conventional transtracheal oxygen tubing 92, best seen in FIG. 7. Oxygen attachment 82 is comprised of a half rounded flexible plastic plug 84 sized for enclosing the open first end 18 of outer cannula 12. Two opposing spring biased clamps 86, similar to clamps 58, are located on the sides of plug 84. Clamps 86 are also designed for releasable attachment to attachment rim 28 of outer cannula 12. Permanently positioned through plug 84 is a small flexible tube or oxygen line 88. Oxygen line 88 enters from the bottom edge of plug 84, curves backward and exits the center domed portion of plug 84, as seen in FIG. 8. A short section of oxygen line 88 projects from the back or domed portion of plug 84, and is referred to as oxygen inner cannula 90. Oxygen inner cannula 90 is positioned inside lumen 24 of outer cannula 12 in use, and extends to the second end 20 thereof, or just slightly beyond. The distal end of oxygen line 88 projecting from the outer bottom edge of plug 84 is structured for releasable attachment to transtracheal oxygen tubing 92 which is generally provided with a portable oxygen tank. The improved features of the immediate invention of the oxygen attachment 82 includes the repositioning of oxygen line 88. In the past art, the transtracheal oxygen tubing 92, or other connecting line, exits horizontally from a tracheostomy mask whereas in the immediate invention, oxygen line 88 exits vertically downward. This provides a very low profile which enables the patient to easily camouflage and conceal the tracheostomy tube assembly 10. High neck sweaters and blouses can be worn without oxygen line 88 and connecting transtracheal oxygen tubing 92 being bent over and kinked, preventing oxygen flow. By allowing the patient to conceal tracheostomy tube assembly 10, he or she can resume a more normal appearance. This can be very important to the patient's mental attitude and overall general recovery. The exposed surface of plug 84 can even be decorated or affixed with jewelry for further concealment if desired.

Another advantage of the improved oxygen attachment 82 is the elimination of open apertures. Plug 84 completely seals the open lumen 24 of outer cannula 12, thus preventing escape of air which would interfere with speech.

Together, all of the components of the immediate invention work in conjunction to eliminate or reduce infections and the pain and discomfort of treating those infections. Overall, the components work as a system to improve the general condition of the patient and promote healing and recovery.

Although I have specifically described the preferred structures of the invention, it should be understood that the specific details are given for example only. Changes in the specific structures described may be made without departing from the scope of my invention, and therefore the scope of my invention is not to be limited by the specification and drawings given for example, but is to be determined by the scope of my appended claims.

What is claimed is:

1. A tracheostomy tube assembly for insertion through an opening into a trachea to help support breathing, comprising:
   an outer cannula having a first end adapted for placement outside a trachea, said outer cannula further having a second end adapted for placement within the trachea,
   means for providing stability of said outer cannula relative to the trachea during use,
   an inner cannula having a first end and a second end, said inner cannula removably inserted into a lumen through said outer cannula,
   connecting means releasably affixing said inner cannula stationary relative to said outer cannula,
   said second end of said inner cannula extending beyond said second end of said outer cannula,
   at least one inflatable cuff affixed to said inner cannula adjacent said second end of said inner cannula, said cuff when inflated within the trachea providing sealing means between the inner wall of the trachea and said second end of said inner cannula,
   means for selectively inflating and deflating said inflatable cuff.

2. A tracheostomy tube assembly according to claim 1 wherein said means for providing stability of said outer cannula relative to the trachea during use, includes a neck plate affixed to said first end of said outer cannula, with said neck plate sized to reside against the outer surface of the neck, said neck plate including strapping means for releasably affixing said neck plate in place against the outer surface of the neck.

3. A tracheostomy tube assembly according to claim 2 wherein both said outer cannula and said inner cannula are slightly curved.

4. A tracheostomy tube assembly according to claim 3 wherein said connecting means releasably affixing said inner cannula stationary relative to said outer cannula includes said first end of said inner cannula releasably affixed to said first end of said outer cannula, with the releasable affixment including at least one movable clamp affixed to said first end of said inner cannula, with said at least one movable clamp structured and positioned to snap over a flange affixed to said first end of said outer cannula.

5. A tracheostomy tube assembly according to claim 4 wherein said neck plate is pivotally affixed to said first end of said outer cannula.

6. A tracheostomy tube assembly according to claim 5 wherein said outer cannula further includes fenestrations.

7. A tracheostomy tube assembly for insertion through an opening into a trachea to help support breathing and allow speech during oxygen therapy utilizing said tracheostomy tube assembly, comprising;
   an outer cannula having a first end adapted for placement outside a trachea, said outer cannula further having a second end adapted for placement within the trachea, said outer cannula being of a type absent inflatable cuffing means, said outer cannula further being sized sufficiently short in length and narrow in diameter so as to allow sufficient air passage to allow speech with said second end placed in the trachea during oxygen therapy, means for providing stability of said outer cannula relative to the trachea during use, a plug releasably and sealingly affixable over an opening in said first end of said outer cannula, an inner cannula affixed to and extending through said plug, a first end of said inner cannula extending through an exterior surface of said plug, means for attaching an oxygen supply hose to said first end of said inner cannula, a second end of said inner cannula terminating in open communication with a lumen of said outer cannula when said plug is affixed over said opening in said first end of said outer cannula.

8. A tracheostomy tube assembly according to claim 7 wherein said means for providing stability of said outer cannula relative to the trachea during use, includes a neck plate affixed to said first end of said outer cannula, with said neck plate sized to reside against the outer surface of the neck, said neck plate including strapping means for releasably affixing said neck plate in place against the outer surface of the neck.

9. A tracheostomy tube assembly according to claim 8 wherein said outer cannula is curved.

10. A tracheostomy tube assembly according to claim 9 wherein the releasable and sealed affixment of said plug to said first end of said outer cannula includes at least one movable clamp affixed to said plug, with said at least one movable clamp structured and positioned to snap over a flange affixed to said first end of said outer cannula.

11. A tracheostomy tube assembly according to claim 10 wherein said neck plate is pivotally affixed to said first end of said outer cannula.

12. A tracheostomy tube assembly according to claim 11 wherein said outer cannula further includes fenestrations.

13. A tracheostomy tube assembly for insertion through an opening into a trachea to help support breathing, comprising in combination:

an outer cannula having a first end adapted for placement outside a trachea, said outer cannula further having a second end adapted for placement within the trachea, means for providing stability of said outer cannula relative to the trachea during use, a respirator inner cannula having a first end and a second end, said respirator inner cannula removably inserted into a lumen through said outer cannula, connecting means releasably affixing said inner cannula stationary relative to said outer cannula, said second end of said respirator inner cannula extending beyond said second end of said outer cannula, at least one inflatable cuff affixed to said respirator inner cannula adjacent said second end of said respirator inner cannula, said cuff when inflated within the trachea providing sealing means between the inner wall of the trachea and said second end of said respirator inner cannula, means for selectively inflating and deflating said inflatable cuff, said respirator inner cannula removable from said outer cannula so as to allow replacement of said respirator inner cannula with a plug, said plug being releasably and sealingly affixable over said opening in said first end of said outer cannula, said plug having an oxygen supply inner cannula affixed to and extending through said plug, a first end of said oxygen supply inner cannula extending through a exterior surface of said plug, means for attaching an oxygen supply hose to said first end of said oxygen supply inner cannula, a second end of said oxygen supply inner cannula positioned to terminate in open communication with said lumen of said outer cannula when said plug is affixed to said first end of said outer cannula.

* * * * *